United States Patent [19]

Olsen

[11] Patent Number: 5,472,000
[45] Date of Patent: Dec. 5, 1995

[54] METHOD AND APPARATUS FOR APPENDAGE RESTRAINT

[76] Inventor: Arlen L. Olsen, 9 Linden Ct., Clifton Park, N.Y. 12065

[21] Appl. No.: 393,099

[22] Filed: Feb. 22, 1995

[51] Int. Cl.⁶ .................................................... A61F 5/37
[52] U.S. Cl. ............................................. 128/878; 128/879
[58] Field of Search ..................................... 128/846, 878, 128/879, 880, DIG. 15; 602/20, 21, 23

[56] References Cited

U.S. PATENT DOCUMENTS

| | | | |
|---|---|---|---|
| 1,596,792 | 8/1926 | Barry | 128/878 |
| 2,450,162 | 9/1948 | Promen. | |
| 2,848,993 | 8/1958 | Terrell. | |
| 3,297,026 | 1/1967 | Van Pelt | 128/878 |
| 3,535,719 | 10/1970 | Murcott. | |
| 3,536,068 | 10/1970 | Stubbs. | |
| 4,422,455 | 12/1983 | Olsen | 128/878 |
| 4,628,925 | 12/1986 | Witzel. | |
| 4,688,564 | 8/1987 | Kelly | 128/878 |
| 4,788,941 | 12/1988 | Villeneuve. | |
| 4,905,713 | 3/1990 | Morante. | |
| 5,076,288 | 12/1991 | Millard | 128/878 |
| 5,345,947 | 9/1994 | Fisher | 128/878 |
| 5,360,019 | 11/1994 | Witzel et al. . | |

*Primary Examiner*—Michael A. Brown
*Attorney, Agent, or Firm*—Schmeiser, Olsen & Watts

[57] ABSTRACT

A device and method for restraining a human appendage is disclosed. The device includes a wrist restraining cushion member, a wrist restraining strap secured to the cushion member and a securement strap secured to the cushion member. The securement strap is attached to a fixed object such as hospital bed for immobilization of the appendage.

5 Claims, 2 Drawing Sheets

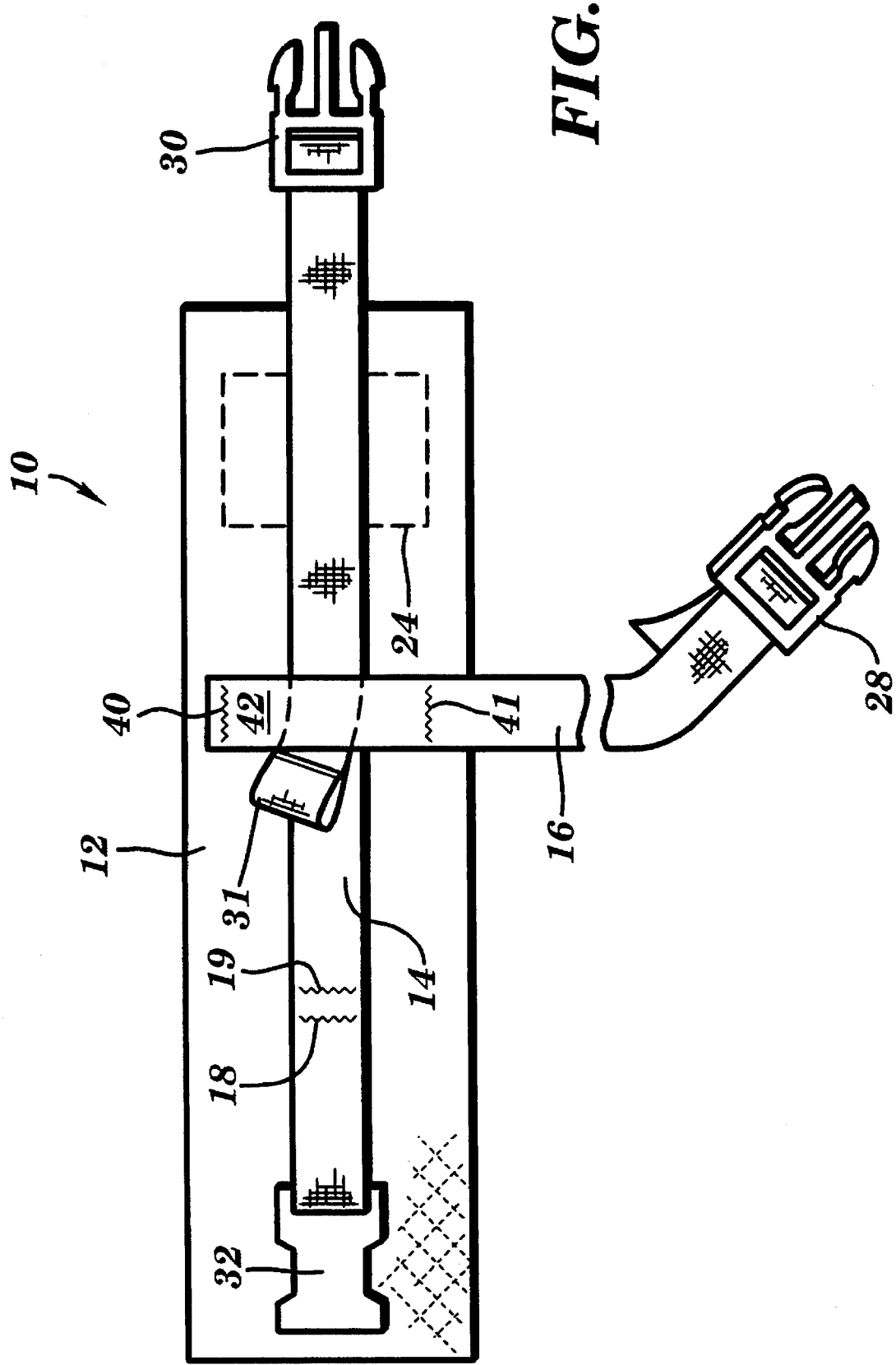

METHOD AND APPARATUS FOR APPENDAGE RESTRAINT

BACKGROUND OF THE INVENTION

The present invention relates to a restraining device for immobilizing a limb of a surgical or psychiatric patient. In particular, the present invention is a quick-release wrist restraining device.

Heretofore, various restraining devices have been used for restraining various portions of the human body. These devices are used to secure a patient to an object such as a hospital bed during surgical operations or recovery therefrom. In addition, these devices are used to restrain psychiatric patients from injuring themselves or others. A disadvantage of many of these devices is that as the surgical or psychiatric patient struggles, the restraining device tightens around the patient's appendage causing loss of circulation to the limb. Another disadvantage is that prior devices include loose hanging straps which may be accessed by a patient's hand for further tightening the restraining device. Also, due to the complex nature of many of these devices, their use and manufacture requires assembly of many parts.

SUMMARY OF THE INVENTION

The present device is a restraining device which includes all the advantages of the prior devices and yet includes none of the disadvantages. The present device includes a restraining device with a plurality of straps which permit restraint of a patient such that when the patient struggles, the device will not tighten and cut off the circulation of the patient's appendage. In addition, the device of the present invention includes a securement device such that loose hanging straps around a cushioning member of the restrainment device may not be accessed by the patient's hands to further tighten the restraining device.

Another advantage of the present invention is ease of manufacture and use. Essentially, three major devices are sewn onto a cushion member of the restraining device of the present invention—a hook and loop fastener, a wrist strap and a securement strap. The hook and loop fastener may be sewn to the cushion member simultaneously with either the wrist-strap or the securement strap. In use, a quick connect connector is used on the wrist and a quick connect connector is used for securement.

The present invention also includes a method of restraining a human wrist which includes providing an elongate cushion member; attaching a first elongate strap to said cushion member at a first attachment location, wherein said first elongate strap includes a tightenable quick-release fastener attached thereto; attaching a second elongate strap to said cushion member at a second attachment location, wherein said second elongate strap includes a quick release fastener; securing said elongate cushion member to said appendage by wrapping said cushion member around said appendage and fastening said tightenable quick-release fastener, and tightening said first elongate strap; and fastening said second elongate strap to an object distal said appendage whereby said appendage is restrained.

BRIEF DESCRIPTION OF THE DRAWINGS

These and other advantages of the present invention will become more readily apparent upon reading the following detailed description and upon reference to the drawings in which:

FIG. 3 is an alternate embodiment of the wrist restraint of the present invention.

DETAILED DESCRIPTION OF THE PREFERRED EMBODIMENT(S)

Figure 1:
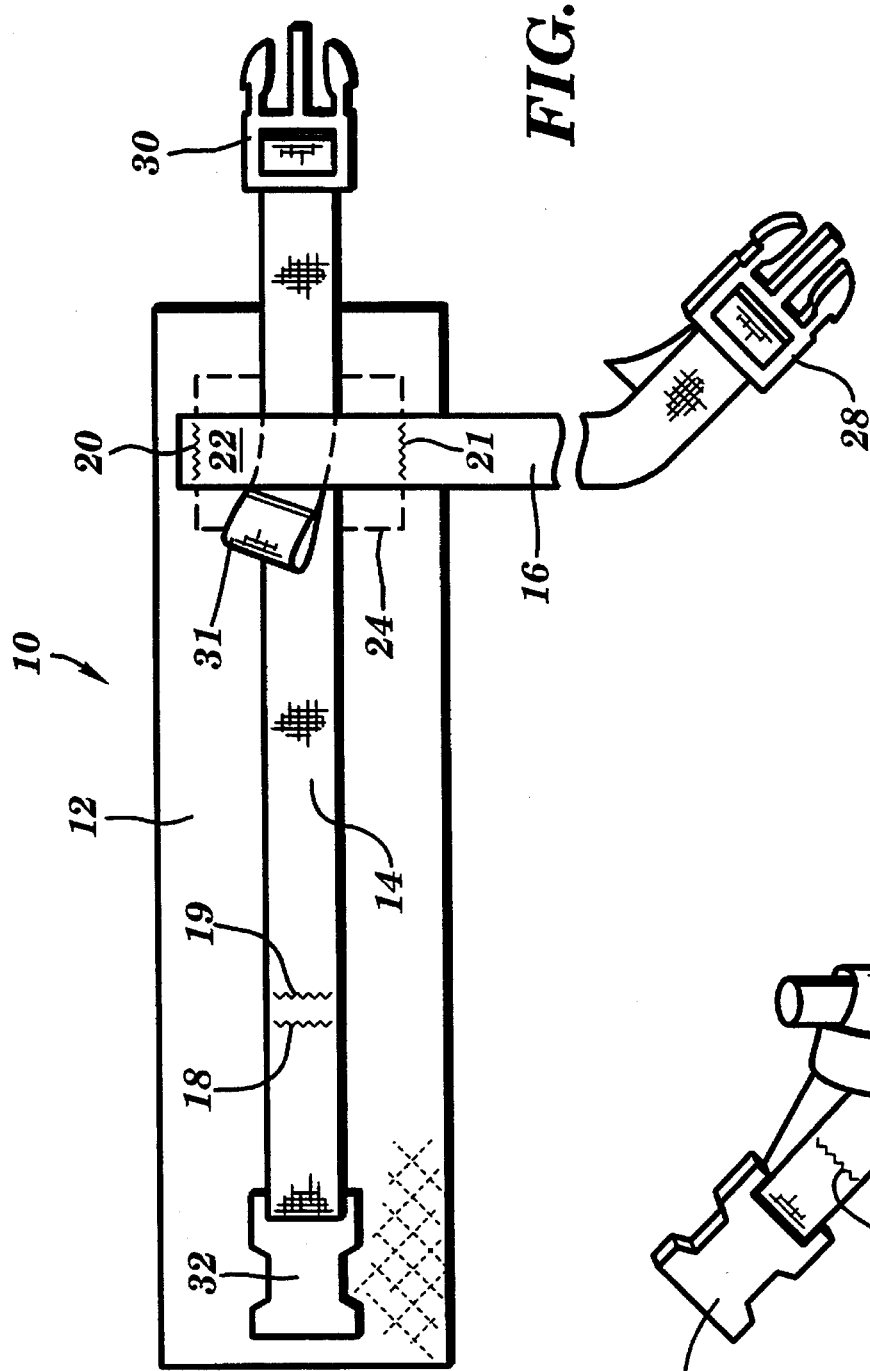
FIG. 1 is top view of the restraining device of the present invention.

FIG. 1 discloses the restraining device 10 of the present invention. The restraining device 10 includes a cushion member 12. The cushion member 12 is made preferably made from a resilient material such as foam rubber surrounded by a fabric coating.

An elongate wrist strap 14 is secured to the cushion member 12 by sewn seams 18, 19. In addition, other securement methods may be used such as a loop, or a plurality of slits through the cushion member 12. Seams 18, 19 provide the advantage of preventing rotation between the cushion member 12 and the wrist strap 14 during tightening of the wrist strap 14. An end of the wrist strap 14 includes a female quick release connector 32 and an opposite side of the wrist strap 14 includes a male quick release connector 30. The wrist strap 14 is tightened by pulling on end portion 31 of the wrist strap 14.

A hook fastener 24 is secured to the cushion member 12 opposite the securement strap 16. The hook fastener may either attach directly to the fabric of the cushion member 12 or to a loop pad (not shown). The loop pad may be provided below female quick release connector 32 for securing the hook fastener 24 when the cushion member 12 is wrapped around a wrist or ankle.

Figure 2:
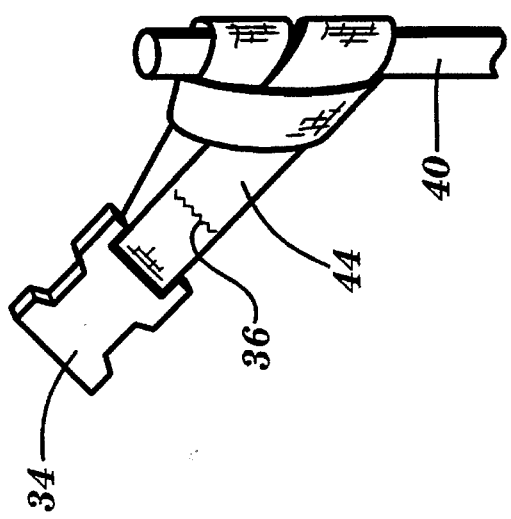
FIG. 2 is a perspective view of a tie down portion the restraining device of the present invention.

Elongate securement strap 16 is attached to the cushion member 12 such that a loop 22 is formed between seams 20, 21. For ease of manufacture, the seams 20, 21 may be sewn simultaneously when the hook fastener 24 is sewn to the cushion member 12 such that the securement strap 16 and the hook fasteners 24 are sewn with a single stitching. Optionally, the securement strap 16 may be sewn at other locations (See FIG. 3) along the cushion member 12 with or without a loop 22. The securement strap 16 includes a male quick release connector 28 at one end thereof. The male quick release connector 28 is attached to a female quick release connector 34 as shown in FIG. 2. The female quick release connector is secured to an fixed object 40 such as a bed frame, bed post, or other stationary object. A strap 44 is looped and sewn at 36. Other types of securement devices may be used other than loops on the strap 44 such as a hook (not shown).

FIG. 3 discloses an alternate embodiment of the restraining device 10. A loop 42 is formed by sewing stitches 40 and 41. The loop is positioned perpendicular to the wrist restraining strap 14.

The foregoing detailed description has been given for clearness of understanding only, and no unnecessary limitations should be understood therefrom, but the appended claims should be construed as broadly as permissible in view of the prior art.

I claim:

1. A method of restraining a human appendage comprising:

providing an elongate cushion member;

attaching a first elongate strap to said cushion member at a first attachment location, wherein said first elongate strap includes a tightenable quick-release fastener attached thereto;

attaching a second elongate strap to said cushion member at a second attachment location such that a loop is formed on said cushion member, wherein said second elongate strap includes a quick release fastener;

securing said elongate cushion member to said appendage by wrapping said cushion member around said appendage and fastening said tightenable quick-release fastener, and tightening said first elongate strap;

inserting said first strap through said loop; and fastening said second elongate strap to an object distal said appendage whereby said appendage is restrained.

2. The method of claim 1, wherein said tightenable releasable fastener is a quick release connector.

3. The method of claim 1, further comprising the step of simultaneously fastening said second securement strap and a hook and loop fastener to said cushioning member.

4. A device for restraining a human appendage comprising:

a wrist restraining cushion member;

a wrist restraining strap secured to said cushion member at a first location, wherein said wrist restraining strap includes a connector attached thereto;

a securement strap secured to said cushion member at a second location displaced from said first location, wherein said securement strap includes a connector attached thereto for attachment of said device to a fixed object and wherein said securement strap forms a loop, whereby, a loose end of said wrist strap may be secured therein.

5. The device of claim 4, wherein said loop is sewn to said cushion member at a location opposite a hook fastener such that seams of the loop securely fasten said hook fastener.

* * * * *